(12) United States Patent
Vakharia et al.

(10) Patent No.: US 8,007,432 B2
(45) Date of Patent: Aug. 30, 2011

(54) ENDOSCOPIC ACCESSORY CONTROL MECHANISM

(75) Inventors: Omar J Vakharia, Cincinnati, OH (US); David Stefanchik, Morrow, OH (US); James T Spivey, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 937 days.

(21) Appl. No.: 11/627,542

(22) Filed: Jan. 26, 2007

(65) Prior Publication Data

US 2008/0183035 A1 Jul. 31, 2008

(51) Int. Cl.
*A61B 1/00* (2006.01)
(52) U.S. Cl. ......... 600/104; 600/106; 600/127; 600/129
(58) Field of Classification Search .................. 600/104, 600/127, 129, 106–107
See application file for complete search history.

(56) References Cited

U.S. PATENT DOCUMENTS

| | | | |
|---|---|---|---|
| 1,891,054 A * | 12/1932 | Pitman | .......................... 606/113 |
| 3,924,608 A | 12/1975 | Mitsui | |
| 4,454,887 A | 6/1984 | Kruger | |
| 4,520,817 A | 6/1985 | Green | |
| 4,646,722 A | 3/1987 | Silverstein et al. | |
| 4,697,576 A | 10/1987 | Krauter | |
| 5,025,778 A | 6/1991 | Silverstein et al. | |
| 5,040,715 A | 8/1991 | Green | |
| 5,201,908 A | 4/1993 | Jones | |
| 5,211,649 A | 5/1993 | Kohler et al. | |
| 5,217,001 A | 6/1993 | Nakao et al. | |
| 5,259,366 A | 11/1993 | Reydel et al. | |
| 5,353,783 A | 10/1994 | Nakao et al. | |
| 5,383,880 A | 1/1995 | Hooven | |
| 5,386,817 A | 2/1995 | Jones | |
| 5,400,770 A | 3/1995 | Nakao et al. | |
| 5,431,322 A | 7/1995 | Green et al. | |
| 5,433,721 A | 7/1995 | Hooven et al. | |
| 5,460,168 A * | 10/1995 | Masubuchi et al. | ........... 600/123 |
| 5,482,197 A | 1/1996 | Green et al. | |

(Continued)

FOREIGN PATENT DOCUMENTS

DE 10139153 A1 2/2003

(Continued)

OTHER PUBLICATIONS

U.S. Appl. No. 11/277,323, filed Mar. 23, 2006, Ortiz et al.
U.S. Appl. No. 11/277,324, filed Mar. 23, 2006, Ortiz et al.
U.S. Appl. No. 11/566,954, filed Dec. 5, 2006, Stefanchik et al.
Paul Breedveld, et al., "A New, Easily Miniaturized Sterrable Endoscope," IEEE Engineering in Medicine and Biology Magazine (Nov./Dec. 2005).

(Continued)

*Primary Examiner* — Matthew J Kasztejna
(74) *Attorney, Agent, or Firm* — Nutter McClennen & Fish LLP

(57) ABSTRACT

Devices and methods useful for manipulating tools at a surgical site are disclosed. In one exemplary embodiment, an accessory device is provided and can include an insertion member and a control wire. The insertion member can have a lumen for receiving a tool therethrough, such as an endoscope. The control wire can be coupled to the insertion member and have a distal portion extending distally from the insertion member and be adapted to receive and to manipulate a tool extending through the insertion member. The control wire can have a wide variety of configurations, and in certain exemplary embodiments the control wire can be slidably received in one or more control wire lumens formed through the insertion member. In use, the control wire can be manipulated, for example by axially sliding the control wire in one or more control wire lumens to control a tool.

20 Claims, 7 Drawing Sheets

U.S. PATENT DOCUMENTS

| | | | |
|---|---|---|---|
| 5,489,256 | A | 2/1996 | Adair |
| 5,503,616 | A | 4/1996 | Jones |
| 5,518,163 | A | 5/1996 | Hooven |
| 5,518,164 | A | 5/1996 | Hooven |
| 5,630,782 | A | 5/1997 | Adair |
| 5,643,175 | A | 7/1997 | Adair |
| 5,651,491 | A | 7/1997 | Heaton et al. |
| 5,667,517 | A | 9/1997 | Hooven |
| 5,715,988 | A | 2/1998 | Palmer |
| 5,749,889 | A | 5/1998 | Bacich et al. |
| 5,762,256 | A | 6/1998 | Mastri et al. |
| 5,779,130 | A | 7/1998 | Alesi et al. |
| 5,782,396 | A | 7/1998 | Mastri et al. |
| 5,823,971 | A * | 10/1998 | Robinson et al. ............ 600/567 |
| 5,865,361 | A | 2/1999 | Milliman et al. |
| 5,944,654 | A | 8/1999 | Crawford |
| 5,954,259 | A | 9/1999 | Viola et al. |
| 6,032,849 | A | 3/2000 | Mastri et al. |
| 6,071,233 | A | 6/2000 | Ishikawa et al. |
| 6,109,500 | A | 8/2000 | Alli et al. |
| 6,179,776 | B1 | 1/2001 | Adams et al. |
| 6,264,087 | B1 | 7/2001 | Whitman |
| 6,315,184 | B1 | 11/2001 | Whitman |
| 6,352,503 | B1 | 3/2002 | Matsui et al. |
| 6,443,973 | B1 | 9/2002 | Whitman |
| 6,458,076 | B1 | 10/2002 | Pruitt |
| 6,522,101 | B2 | 2/2003 | Malackowski |
| 6,527,753 | B2 | 3/2003 | Sekine et al. |
| 6,569,085 | B2 | 5/2003 | Kortenbach et al. |
| 6,699,180 | B2 | 3/2004 | Kobayashi |
| 6,716,233 | B1 | 4/2004 | Whitman |
| 6,740,030 | B2 | 5/2004 | Martone et al. |
| 6,761,685 | B2 | 7/2004 | Adams et al. |
| 6,786,864 | B2 | 9/2004 | Matsuura et al. |
| 6,790,173 | B2 | 9/2004 | Saadat et al. |
| 6,793,652 | B1 | 9/2004 | Whitman et al. |
| 6,808,491 | B2 | 10/2004 | Kortenbach et al. |
| 6,824,509 | B2 * | 11/2004 | Yamaya et al. ............. 600/106 |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,878,106 | B1 | 4/2005 | Herrmann et al. |
| 6,984,203 | B2 | 1/2006 | Tartaglia et al. |
| 6,997,931 | B2 | 2/2006 | Sauer et al. |
| 7,029,435 | B2 | 4/2006 | Nakao |
| 7,056,284 | B2 | 6/2006 | Martone et al. |
| 7,070,559 | B2 | 7/2006 | Adams et al. |
| 7,087,010 | B2 | 8/2006 | Ootawara et al. |
| 7,226,410 | B2 * | 6/2007 | Long ............................ 600/114 |
| 7,351,202 | B2 * | 4/2008 | Long ............................ 600/106 |
| 2002/0049454 | A1 | 4/2002 | Whitman et al. |
| 2002/0107530 | A1 | 8/2002 | Sauer et al. |
| 2002/0183591 | A1 | 12/2002 | Matsuura et al. |
| 2003/0036679 | A1 | 2/2003 | Kortenbach et al. |
| 2003/0130561 | A1 | 7/2003 | Suzuki et al. |
| 2003/0130564 | A1 | 7/2003 | Martone et al. |
| 2003/0176766 | A1 | 9/2003 | Long et al. |
| 2003/0176767 | A1 | 9/2003 | Long et al. |
| 2003/0176880 | A1 | 9/2003 | Long et al. |
| 2003/0195387 | A1 | 10/2003 | Kortenbach et al. |
| 2003/0208219 | A1 | 11/2003 | Aznoian et al. |
| 2004/0133075 | A1 | 7/2004 | Motoki et al. |
| 2004/0215058 | A1 | 10/2004 | Zirps et al. |
| 2004/0230095 | A1 | 11/2004 | Stefanchik et al. |
| 2004/0230096 | A1 | 11/2004 | Stefanchik et al. |
| 2004/0230097 | A1 | 11/2004 | Stefanchik et al. |
| 2005/0049455 | A1 | 3/2005 | Ootawara et al. |
| 2005/0119524 | A1 | 6/2005 | Sekine et al. |
| 2005/0119525 | A1 | 6/2005 | Takemoto |
| 2005/0124855 | A1 | 6/2005 | Jaffe et al. |
| 2005/0131278 | A1 | 6/2005 | Dickopp |
| 2005/0137454 | A1 | 6/2005 | Saadat et al. |
| 2005/0137455 | A1 | 6/2005 | Ewers et al. |
| 2005/0149067 | A1 | 7/2005 | Takemoto et al. |
| 2005/0154258 | A1 | 7/2005 | Tartaglia et al. |
| 2005/0165419 | A1 | 7/2005 | Sauer et al. |
| 2005/0177181 | A1 | 8/2005 | Kagan et al. |
| 2005/0222495 | A1 | 10/2005 | Okada et al. |
| 2005/0234297 | A1 | 10/2005 | Devierre et al. |
| 2005/0256374 | A1 | 11/2005 | Long et al. |
| 2006/0015009 | A1 | 1/2006 | Jaffe et al. |
| 2006/0020247 | A1 | 1/2006 | Kagan et al. |
| 2006/0079735 | A1 | 4/2006 | Martone et al. |
| 2006/0235271 | A1 | 10/2006 | Carter et al. |
| 2006/0258903 | A1 | 11/2006 | Stefanchik et al. |
| 2006/0258904 | A1 | 11/2006 | Stefanchik et al. |
| 2006/0259010 | A1 | 11/2006 | Stefanchik et al. |

FOREIGN PATENT DOCUMENTS

| | | |
|---|---|---|
| EP | 1 847 78 | 6/1986 |
| EP | 0 552 050 | 7/1993 |
| EP | 0 552 423 | 7/1993 |
| EP | 0 634 144 | 1/1995 |
| EP | 0 705 570 | 4/1996 |
| EP | 0 880 338 | 12/1998 |
| EP | 1 152 685 | 8/2000 |
| EP | 1 161 174 | 9/2000 |
| EP | 1 284 120 | 2/2003 |
| EP | 1 400 214 | 3/2004 |
| EP | 1 402 837 | 3/2004 |
| EP | 1 426 012 | 6/2004 |
| EP | 1 459 695 | 9/2004 |
| EP | 1 535 565 | 6/2005 |
| EP | 1582138 | 10/2005 |
| EP | 1 593 337 | 11/2005 |
| EP | 1 607 050 | 12/2005 |
| GB | 2109241 | 6/1983 |
| GB | 2272159 | 5/1994 |
| JP | 2000033071 | 2/2000 |
| JP | 2000171730 | 6/2000 |
| JP | 2000325303 | 11/2000 |
| JP | 2002143078 | 5/2002 |
| JP | 2005131107 | 5/2005 |
| JP | 2005131163 | 5/2005 |
| JP | 2005131164 | 5/2005 |
| JP | 2005131173 | 5/2005 |
| JP | 2005131211 | 5/2005 |
| JP | 2005131212 | 5/2005 |
| JP | 2005137423 | 6/2005 |
| JP | 2005152416 | 6/2005 |
| JP | 2005304586 A | 11/2005 |
| WO | WO-91/14391 | 10/1991 |
| WO | WO-97/29680 | 8/1997 |
| WO | WO-00/48506 | 8/2000 |
| WO | WO-00/54653 | 9/2000 |
| WO | WO-00/72762 | 12/2000 |
| WO | WO-00/72765 | 12/2000 |
| WO | WO-01/49165 | 7/2001 |
| WO | WO-01/56457 | 8/2001 |
| WO | WO-01/89624 | 11/2001 |
| WO | WO-02/43571 | 6/2002 |
| WO | WO-03/000138 | 1/2003 |
| WO | WO-03/015604 | 2/2003 |
| WO | WO-03/077769 | 9/2003 |
| WO | WO-2004/021868 | 3/2004 |
| WO | WO-2004/034875 | 4/2004 |
| WO | WO-2004/047626 | 6/2004 |
| WO | WO-2004/052426 | 6/2004 |
| WO | WO-2004/096015 | 11/2004 |
| WO | WO-2004/103157 | 12/2004 |
| WO | WO-2004/105593 | 12/2004 |
| WO | WO-2005/016181 | 2/2005 |

OTHER PUBLICATIONS

Frederick Van Meer, et al., "A Disposable Plastic Compact Wrist for Smart Minimally Invasive Surgical Tools," LAAS/CNRS, this paper appears in : Intelligent Robots and Systems, 2005. (IROS 2005). 2005 IEEE/RSJ International Conference on Aug. 2-6, 2005.

International Search Report issued Jul. 1, 2008 in PCT Appln. No. PCT/US2008/051902, 8 pages.

The International Search Report and The Written Opinion of the International Searching Authority dated Oct. 20, 2008 for PCT Application No. PCT/US2008/051902 (16 pages).

* cited by examiner

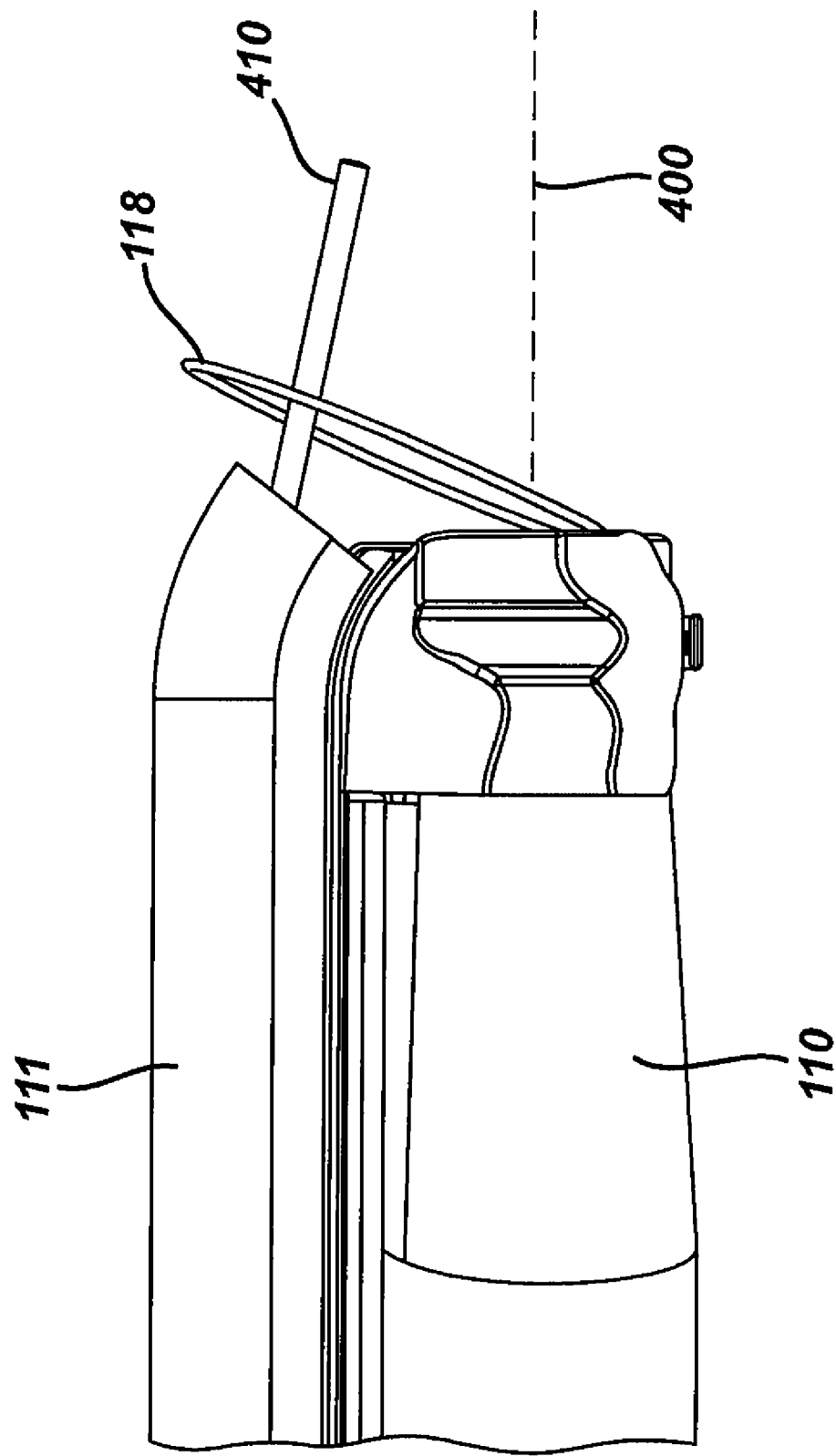

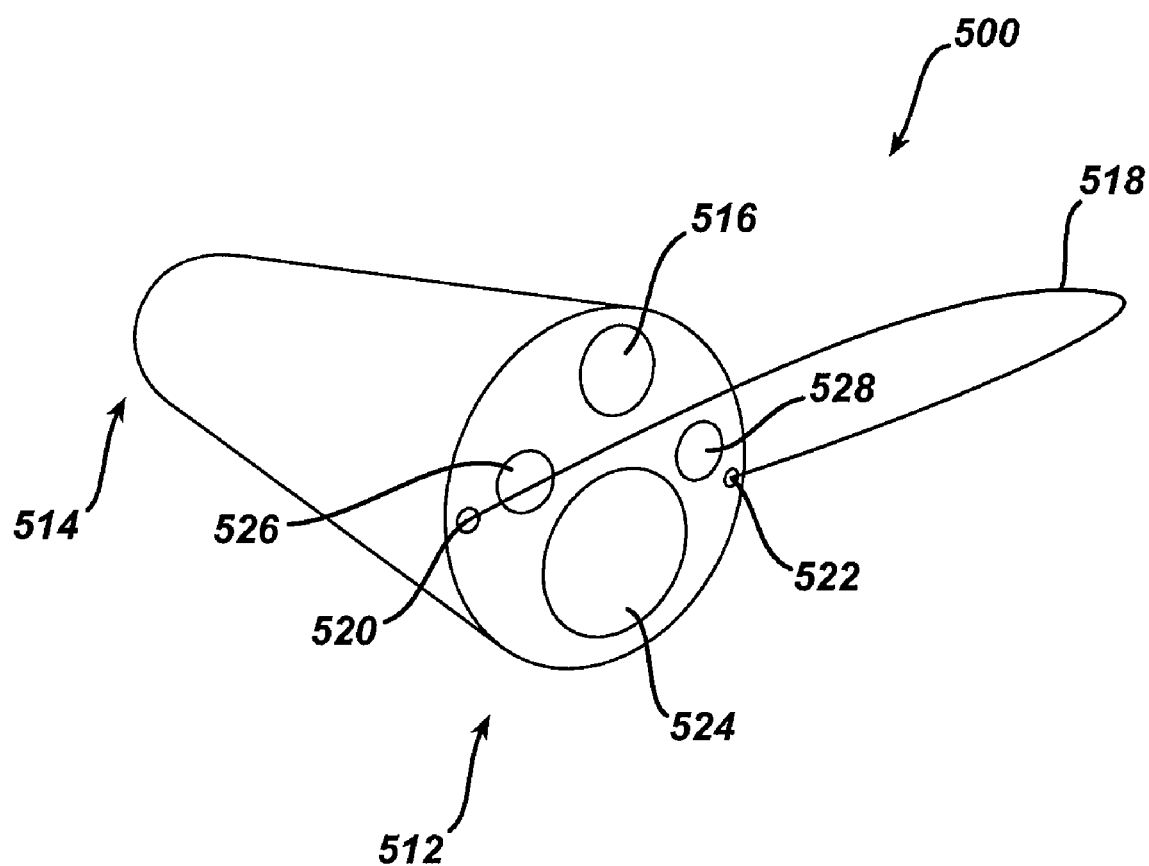

ENDOSCOPIC ACCESSORY CONTROL MECHANISM

FIELD OF THE INVENTION

The present invention generally relates to methods and devices for manipulating tools at a surgical site.

BACKGROUND OF THE INVENTION

Endoscopic surgical devices are often preferred over traditional open surgical devices because the use of a natural orifice tends to reduce post-operative recovery time and complications. Consequently, significant development has gone into a range of endoscopic surgical devices that are suitable for precise placement of a working end of a tool at a desired surgical site through a natural orifice. These tools can be used to engage and/or treat tissue in a number of ways to achieve a diagnostic or therapeutic effect.

The ability to manipulate a tool at a surgical site can be limited. For example, the devices and methods used to place a tool may restrict its movement relative to the surgical site, to an endoscope, or to other tools. At the same time, many endoscopic procedures require that surgical tools be positioned or used independently at the surgical site. For example, oftentimes it is desirable that an endoscope provide a view of a surgical site and/or the distal end of a surgical tool. The view of the endoscope may be limited to nearby objects within a small viewable area in front of the endoscope and require manipulation of the endoscope and/or the surgical tool in order to obtain an adequate view. A procedure may also call for the cooperative use of two or more surgical tools and may necessitate precise placement and orientation of such tools with respect to one another. For example, one tool may be employed to manipulate or grasp tissue while another tool dissects the tissue.

Accordingly, there is a need for improved methods and devices for viewing and/or manipulating tools at a surgical site.

SUMMARY OF THE INVENTION

In one embodiment, an accessory device is provided having an insertion member and a control wire. The insertion member can include at least one lumen adapted to receive a tool therethrough and can further include at least one control wire lumen formed therein and adapted to slidably receive the control wire. In one embodiment, the insertion member can have first and second control wire lumens adapted to slidably receive the control wire, and a distal portion of the control wire can be disposed between distal ends of the first and second control wire lumens. In certain exemplary embodiments, the insertion member can be in the form of an elongate sheath with a lumen extending longitudinally between proximal and distal ends thereof for receiving an endoscope and can also include an accessory channel extending longitudinally along the elongate sheath and having a lumen extending longitudinally therethrough for receiving a tool. The accessory device can optionally further include a control mechanism disposed on a handle coupled to a proximal end of the insertion member and operatively associated with the control wire for axially moving the control wire.

The control wire can have a variety of configurations. In one exemplary embodiment, the control wire can be coupled to the insertion member and it can have a distal portion extending distally from the insertion member adapted to receive and manipulate a tool extending from the insertion member. The distal portion of the control wire extending distally from the insertion member can have a variety of shapes. For example, the distal portion of the control wire can be in the form of an arc, or it can include a loop formed therein adapted to receive a tool therethrough. The control wire can also be adapted to move in a variety of ways. In one embodiment, the control wire can be adapted to move at least a distal end of a tool extending through the insertion member into a viewing window of an endoscope disposed through the insertion member, or in some cases, a viewing window distal to an elongate sheath adapted for receiving an endoscope. The control wire can also be adapted to move a distal end of a tool extending through the insertion member laterally with respect to a longitudinal axis of the insertion member, and/or to push a distal end of a tool extending through the insertion member distally away from the insertion member.

Also provided is an endoscopic system, which in one embodiment can have an elongate sheath and an engagement mechanism. The elongate sheath can have a first lumen extending longitudinally between proximal and distal ends thereof for receiving an endoscope. The elongate sheath can also include at least one engagement mechanism lumen formed therethrough and adapted to slidably receive the engagement mechanism. In an exemplary embodiment, the elongate sheath can include first and second engagement mechanism lumens and a distal portion of the engagement mechanism can extend between distal ends of the first and second engagement mechanism lumens. In other embodiments, an accessory channel can be provided and the accessory channel can be coupled to the elongate sheath and it can be adapted to receive a tool therethrough.

In other aspects, a method for positioning a tool is provided and in one embodiment includes advancing a tool longitudinally along an endoscope to position a distal end of the tool through an opening formed by a control wire extending distally from the endoscope, and manipulating the control wire to move the tool relative to the endoscope. The distal end of the tool can also be inserted through a loop formed in the control wire. In some embodiments, the tool can be advanced through a lumen formed in an accessory channel that is coupled to the endoscope, and/or the endoscope can be inserted through a body lumen prior to advancing the tool.

The control wire can be manipulated using a variety of techniques. In one embodiment, manipulating the control wire can include axially sliding the control wire through a control wire lumen disposed longitudinally along the endoscope. Manipulating the control wire can also include axially moving the control wire through the control wire lumen in the elongate sheath through which the endoscope is disposed and which has the control wire lumen formed therein. In certain embodiments, axially moving the control wire can include rotating a knob coupled to the control wire and disposed on a handle at a proximal end of the elongate sheath. The control wire can move the tool in a variety of ways. In one exemplary embodiment, the control wire can pull the distal end of the tool into a viewing window of the endoscope. In other embodiments, the control wire can push the distal end of the tool distally away from the distal end of the endoscope, and/or can move the distal end of the tool laterally with respect to a longitudinal axis of the endoscope.

BRIEF DESCRIPTION OF THE DRAWINGS

The invention will be more fully understood from the following detailed description taken in conjunction with the accompanying drawings, in which:

FIG. 4 is a side view of a distal portion of the accessory device shown in FIG. 1 with a tool disposed in the accessory channel;

FIG. 5 is a perspective view of an exemplary endoscope having a control wire coupled thereto;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods useful for manipulating and/or viewing tools at a surgical site. In some cases access to the surgical site can be gained translumenally, e.g., through a body lumen and/or a natural orifice in the body. The devices and methods are particularly useful for manipulating and viewing tools at the working end of a viewing instrument such as an endoscope. Although some of the embodiments disclosed herein will be described in the context of an endoscopic procedure, the devices and methods are not limited to such applications. They may be used with a wide variety of viewing instruments and other tools. Moreover, they may be used in a wide range of other procedures including non-endoscopic procedures, such as laparoscopic and open procedures, and in virtually any medical procedure now or later in use.

Figure 1:
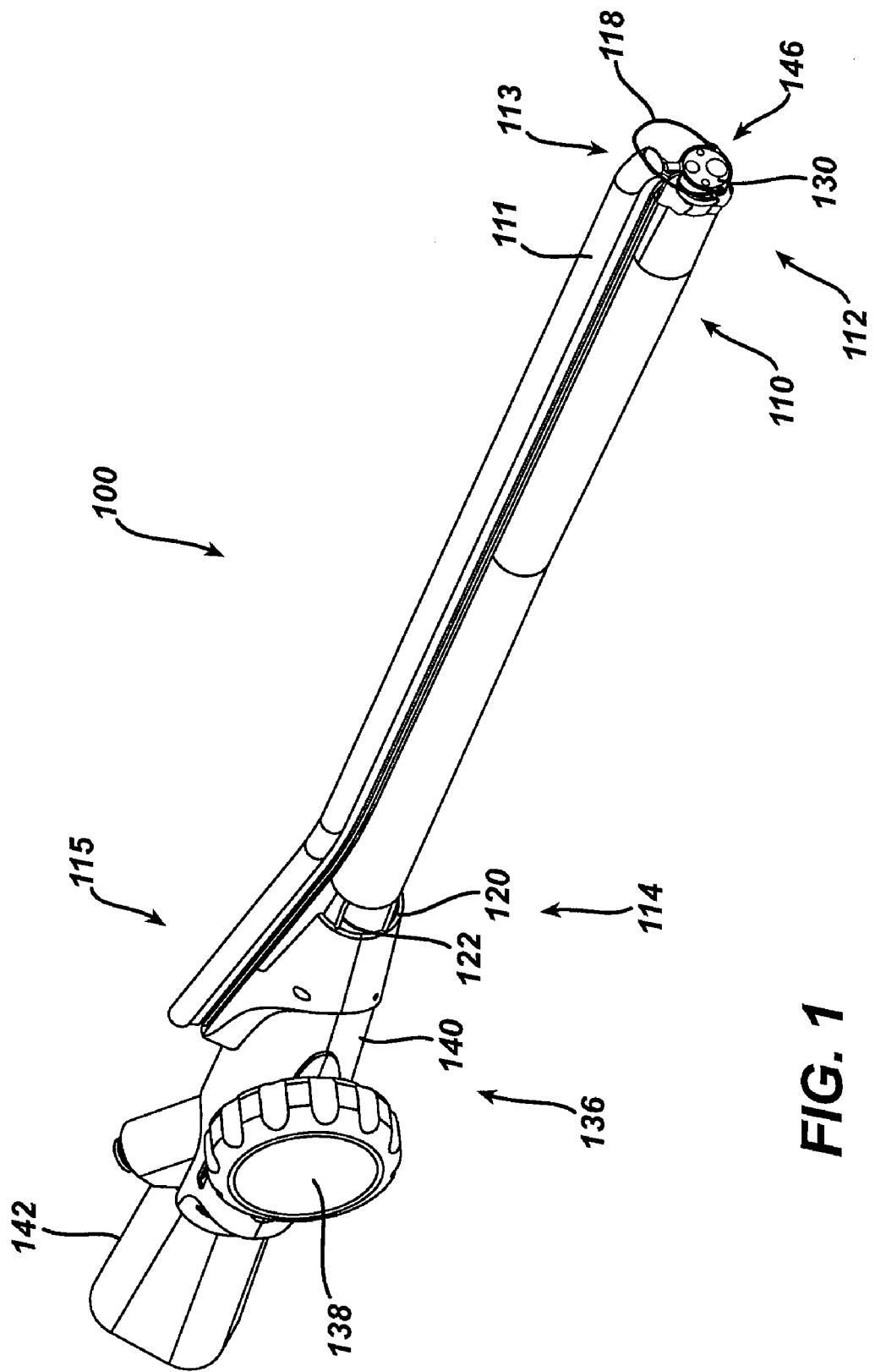
FIG. 1 is a perspective view of one exemplary embodiment of an accessory device having an elongate sheath with a control wire coupled thereto and an endoscope extending therethrough, and an accessory channel.
Figure 2:
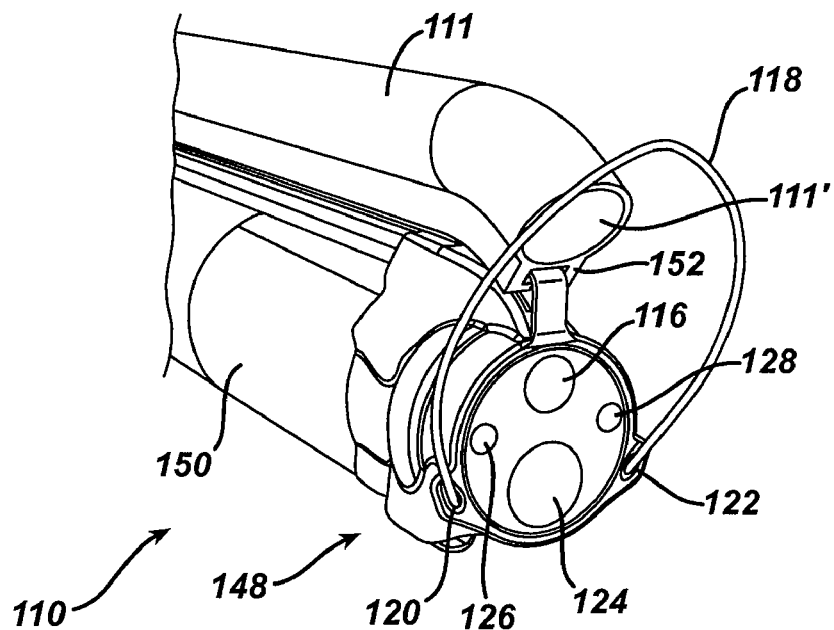
FIG. 2 is an enlarged view of a distal portion of the accessory device shown in FIG. 1.
Figure 3:
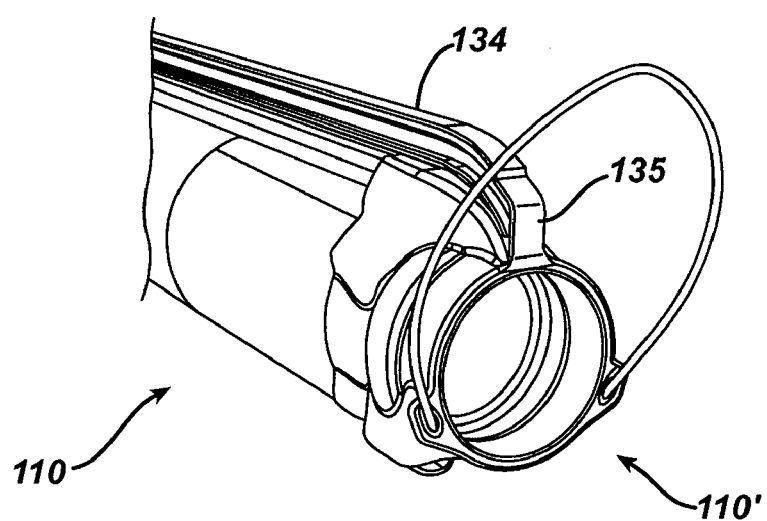
FIG. 3 is an enlarged view of a distal portion of the accessory device shown in FIG. 1 with the accessory channel and endoscope removed.

FIGS. 1-3 illustrate one exemplary embodiment of an accessory device 100. The accessory device 100 can have a variety of configurations, but in the illustrated embodiment the accessory device 100 includes an insertion member in the form of an elongate sheath 110 and an accessory channel 111. As shown, the elongate sheath 110 has a distal end 112 with a control wire 118 coupled thereto and a proximal end with a handle 142 and a control mechanism 136 coupled thereto.

The elongate sheath 110 can have a tool such as an endoscope 130 disposed therethrough. The distal face 146 of the endoscope 130 can have a viewing instrument 124, for example a lens, one or more lighting elements 126, 128, for example lights or fiber optics, and a lumen 116 formed therein for receiving one or more tools, such as viewing instruments, graspers, cutting devices, irrigation devices, and so on. The elongate sheath 110 can also have a mating element such as a track 134 for mating with a complementary mating element formed on the accessory channel 111, such as a rail 152. In addition, the elongate sheath 110 can have one or more control wire lumens 120, 122 formed therein and extending between the proximal and distal ends 112, 114 thereof. The control wire 118 can be slidably disposed in the control wire lumens 120, 122. The control mechanism 136 can be coupled to the control wire 118 and can be adapted to move the control wire 118, for example, by manipulation of a knob 138. Movement of the control wire 118 can include, for example, axially sliding the control wire 118 within one or both of the control wire lumens 120, 122 or axially rotating the control wire 118. In use, movement of the control wire 118 can be effective to manipulate a tool. The tool, for example, can extend distally from the lumen 116 in the endoscope 130, or from the accessory channel 111, or the tool can be separate from or spaced apart from the elongate sheath 110. The manipulation can take many forms, but as one example, a portion of the tool can be pulled into a viewing window of the endoscope 130.

The elongate sheath 110 can have a variety of configurations, but as shown in FIG. 1 and with more detail in FIGS. 2-3, the elongate sheath 110 includes an elongate tube or shaft 150 having a lumen 110' formed therein and adapted to receive a tool such as an endoscope 130 therethrough. The shaft 150 can have a proximal end 114 adapted to remain outside of the body and a distal end 112 adapted to be positioned within the body and adjacent to a surgical site. The shaft 150 can have any cross-sectional shape, including circles, rectangles, squares, ovals, ellipses, and so on. In addition, the shaft 150 can have an optional end cap 148, as shown in FIGS. 1-2. While illustrated as circular in FIGS. 1-2, the interior of the lumen 110' can be of any shape suitable to receive a tool. The lumen 110' can be adapted to receive a tool such as an endoscope 130, for example as a covering or sleeve, such that the distal end of the endoscope 130 is disposed at the distal end 112 of the elongate sheath 110 for viewing a surgical site. The lumen 110' or portions thereof can also be rigid and/or have a fixed diameter for passing tools therethrough. The elongate sheath 110 can also include any number of additional lumens for receiving one or more tools therethrough, including, for example, a tool to be used with an endoscope received through lumen 110'. The elongate sheath 110 or portions thereof can be flexible. The elongate sheath 110 can be made of a flexible material or can include articulating segments placed in desired locations to provide a desired degree of suppleness. A flexible elongate sheath 110 can be advantageous in some applications, for example, where it is desired to advance the elongate sheath 110 through a tortuous body lumen or to create an elastic fit with a tool received in a lumen. A flexible elongate sheath 110 can also accommodate articulation or steering of a tool disposed therethrough, such as an endoscope with an articulating distal end. As previously mentioned, the elongate sheath 110 can also include one or more control wire lumens 120, 122 formed therein and extending between the distal end 112 and the proximal end 114 of the elongate sheath 110. The control wire lumens 120, 122 can be adapted to receive one or more control wires 118 therein. Moreover, as shown in FIGS. 1-2, the control wire lumens 120, 122 of the elongate sheath 110 can be configured to orient the control wire in a desired direction or angle. For example, the control wire lumens 120, 122 can be bent or angled at the distal end 112 of the elongate sheath 110 such that the control wire exits the elongate sheath 110 at an desired angle. The control wire lumens 120, 122 can also include a groove formed therein, or an asymmetrical internal shape such as a ramp structure formed within the interior of the control wire lumen 120, 122. as shown, the control wire lumens 120, 122 are configured such that the control wire 118 extends at an upward angle from the distal end 112 of the elongate sheath 110. Such an arrangement is advantageous for allowing the control wire 118 to reach and/ or manipulate a tool extending through lumen 116 or through the accessory channel 111. It will be apparent to one skilled in the art that the control wire lumens 120, 122 as well as lumens adapted for receiving tools, can be internal or external to the elongate sheath 110. For example, in FIGS. 1-2 the elongate sheath 110 has control wire lumens integrally formed within the end cap 148 and internal to the elongate sheath 110. Alternatively, the control wire lumens 120, 122 can be formed on an exterior surface of the elongate sheath 110, e.g., as a tube or coil pipe fixedly or removably attached to and extending between proximal and distal ends 112, 114 of the elongate sheath 110. The elongate sheath 110 can also include one or more fixed attachment points for the control wire 118, any of which can replace or supplement the control wire lumens 120, 122. An attachment point at the distal end 112 of the elongate sheath 110 can replace control lumen 122, for example, so that the control wire 118 extends from the attachment point to the control wire lumen 120.

The accessory channel 111 can have a variety of configurations. In FIGS. 1-3, the accessory channel 111 is shown as an elongate tube having a proximal end 115 and a distal end 113. The accessory channel 111 can have any length, including a same or a similar length as the elongate sheath 110. The accessory channel 111 can have virtually any cross-sectional shape, including those shapes mentioned previously with respect to the elongate shaft 110. In the illustrated embodiment, the accessory channel 111 has a circular cross-sectional shape that is smaller in diameter than that of the elongate sheath 110. However, the accessory channel 111 need not have any particular size relative to the elongate sheath 110 and can have a size, including a diameter, width, or other dimension, equal to, greater than or less than that of the elongate sheath 110. The accessory channel 111 can have a lumen 111' formed therein for receiving a tool or material therethrough. Multiple lumens are possible, such as was described previously with respect to the elongate sheath 110. The accessory channel 111 or portions thereof can be flexible or configured with articulating segments, which can be advantageous if the elongate sheath 110 is also flexible, as such an arrangement can allow for the elongate sheath 110 to be flexible even when the accessory channel 111 is mated to the elongate sheath 110. A distal portion of the accessory channel can also be adapted to be controllably articulated, as described in commonly owned U.S. patent application Ser. No. 11/277,324, entitled "Articulating Endoscopic Accessory Channel," of James T. Spivey et al., which is hereby incorporated by reference in its entirety.

As previously mentioned, the elongate sheath 110 and the accessory channel 111 each can have a mating element formed thereon and the mating elements can be adapted to mate with one another. The mating elements can have a variety of configurations, including for example interlocking elements, engaging elements, complementary shapes, sliding members, magnetic elements, spring-loaded retaining members, elastic members, and so on. Such elements can be formed on any portion of or along the entire length of the elongate sheath 110 and/or accessory channel 111. As illustrated in FIG. 3 the mating element formed on the elongate sheath 110 is a track 134 disposed longitudinally along an outer surface of the elongate sheath 110 between proximal and distal ends 112, 114 thereof. The track 134 can have virtually any length, although it can be advantageous if the track 134 is comparable in length to the elongate sheath 110 so that that accessory channel 111 can be securely mated thereto. As shown, the track 134 can define a protruding surface which can be adapted to complement and accommodate the mating element of the accessory channel 111. The mating element of the accessory channel 111, as shown in FIGS. 1-2, is a C-shaped rail 152. The rail 152 can be disposed longitudinally on an exterior surface of the accessory channel 111 between proximal and distal ends 113, 115 thereof. The rail 152 can have virtually any length, including a length differing from the length of the track 134. The track 134 and the rail 152 can be adapted to slide when mated, e.g., to allow the rail 152 to be advanced distally or withdrawn proximally along the track 134 when mated. In such a case, the mating surfaces of the track 134 and the 152. However, it also possible that the track 134 have a notched, indented, or serrated channel 152 to facilitate movement of the rail 152 between selectable positions. In another embodiment, the track 134 can include an end cap 135 to prevent the distal end of the rail 152 from advancing beyond the distal end of the track 134. In other embodiments, one or more of the track 134 and rail 152, or other mating elements, can be rigid, semi-flexible, or flexible. A flexible track 134 and/or rail 152 can be advantageous in some applications, such as where the elongate shaft and/or accessory channel are flexible, or where it is desired that the track 134 and the rail 152 have an elastic fit, e.g., where the track 134 elastically encases and/or releases the rail 152. The locations of the track 134 and the rail 152 can also be reversed, e.g., the track 134 being disposed on the accessory channel 111 and the rail 152 being disposed on the elongate sheath 110.

As one skilled in the art will understand, the accessory device 100 need not include an accessory channel 111. For example, the insertion member can be in the form of an elongate sheath 110 with a control wire 118 coupled thereto, as previously described. In such a case, the elongate sheath 110 need not include a mating element such as a track 134 adapted for mating to the accessory channel 111. In use, movement of the control wire 118 can be effective to manipulate a tool extending distally from a lumen formed in an endoscope, such as the lumen 116 in the endoscope 130 shown in FIG. 1. Further, one skilled in the art will also understand that it is not necessary to include an elongate sheath 110 or an accessory channel 111. For example, as shown in FIG. 5, an alternate embodiment of an accessory device 500 can have an insertion member in the form of an endoscope 500. As shown, a lumen 516 is formed in the endoscope 500 for receiving a tool therethrough and the distal end 512 of the endoscope 510 has a viewing element 524 and a first and second lighting elements 526, 528. The endoscope 510 has a first and second control wire lumens 520, 522 formed therein. In use, the control wire 518 can be moved to manipulate a tool extending distally from the lumen 518 and/or a tool adjacent to the accessory device 500, such as another tool disposed at the surgical site.

As previously mentioned, the accessory device 100 of FIG. 1 can also have a control wire 118. The control wire 118 can have a variety of configurations, but as shown, the control wire 118 is a solid wire. The control wire 118 can be flexible or rigid. While a flexible control wire 118 can be advantageous to aid movement of the control wire 118 within the control wire lumens 120, 122, a rigid control wire 118 can be advantageous for pushing or otherwise manipulating a tool at a surgical site. The control wire 118 can be made of any material suitable for use within the body, including stainless steel, and/or a titanium alloy such as nitinol, and can be constructed in a variety of ways. For example, the control wire 118 can be a single wire, or can be formed of braided or twisted wires or fibers. The control wire 118 can also have a coating or surface treatment for aiding in movement, e.g., a bio-compatible lubricant or a resin such as a Teflon® coating. The properties desired in the control wire 118, such as its rigidity, flexibility, malleability, and so on can inform the composition and/or configuration of the control wire 118, as one skilled in the art will recognize.

Figure 6A:
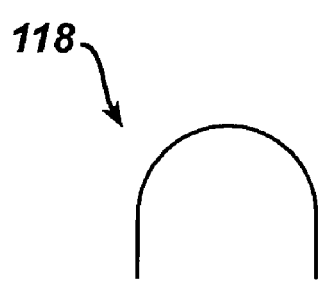
FIG. 6A is a top view of the control wire shown in FIG. 1.
Figure 6B:
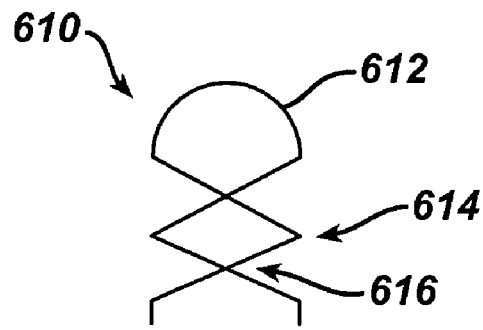
FIG. 6B is a top view of an alternate embodiment of a control wire having an opening formed therein.
Figure 6C:
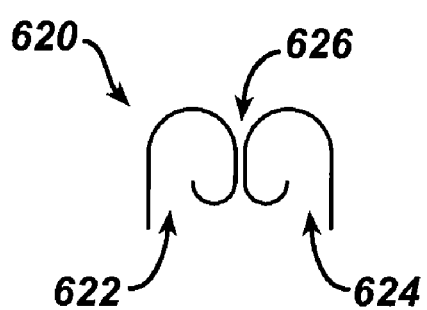
FIG. 6C is a top view of another embodiment of a control wire having two curved portions formed therein.

The control wire 118 can have a variety of shapes formed therein, but as shown in FIG. 1 and in an isolation view in FIG. 6A, the control wire 118 forms an arc between the distal ends of the lumens 120, 122 and thus a tool can be received between the control wire 118 and the distal end 112 of the elongate sheath 110. The arc can have virtually any size and can be formed by flexing the control wire 118 between the lumens 120, 122 or the arc can be prefabricated, e.g., such that the control wire 118 retains an arc shape even when removed from the lumens 120, 122. The shape of the control wire 118 can vary widely, and include hooks, curves, loops, barbs, rectangles, squares, etc. For example, FIG. 6B illustrates an alternate embodiment of a control wire 610 having a loop 612 formed therein and a cross-hatch pattern 614. The control wire 610 can receive a tool therethrough (e.g., through loop 612) and can be used to push the tool distally away from the elongate sheath 110 and/or and endoscope 130 received therethrough, as will be discussed in more detail below. Each intersection point 616 formed in the control wire 610 can be unattached to allow for movement or can be fixedly attached together, for example by adhesive or solder or welding, for stiffening the control wire 610. FIG. 6C illustrates another embodiment of a control wire 620 having a first hook 622 and an opposing second hook 624. With such a configuration a first tool can be received in the first hook 622 while a second tool can be received in the second hook 624. As shown, the hooks 622, 624 are not connected and can be moved independently; however, the hooks 622, 624 can be joined at point 626 to allow the hooks 622, 624 to move in conjunction with one another.

Figure 6D:
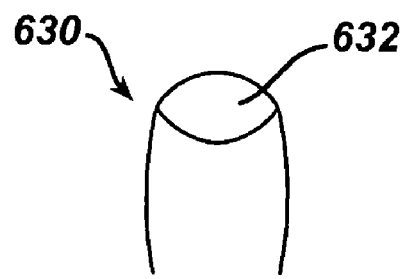
FIG. 6D is a top view of another embodiment of a control wire having an opening formed therein.

FIG. 6D illustrates yet another embodiment of a control wire 630 having a loop 632 formed therein and adapted to receive one or more tools therethrough. The control wire 118 can have virtually any length. For example, as shown in FIG. 1, the control wire 118 can extend from the proximal control mechanism 136 to the distal end 112 of the elongate sheath 110, extend distally from a first control wire lumen 120 to a second control wire lumen 122 at the distal end 112 of the elongate sheath 110, and extend back to the proximal control mechanism 136 in a second control wire lumen 122. Alternatively, the control wire 118 can extend partway along one or more control wire lumens 120, 122 and have a coupling to the control mechanism 136 via an intermediary rod, cable, or actuator. The control wire 118 can also be fixed at one or more previously mentioned optional attachment points on the elongate sheath 110 instead of extending through a control wire lumen 120, 122. As previously mentioned, in some embodiments the control wire lumens 120, 122 can be configured to direct the control wire 118 at an angle relative to the longitudinal axis of the elongate sheath 110; however, the control wire 118 can also be adapted to extend at any angle relative to the accessory device 100. For example, the control wire 118 have one or more bends or angles formed therein. The extent of the bend or angle can be of any size, but it can be advantageous if the bend or angle is sufficiently large to allow a tool extending distally from the elongate sheath 110 to be received between the distal end of the elongate sheath 110 and the control wire 118, or, alternatively, in a loop formed in the control wire 118.

Figure 7:
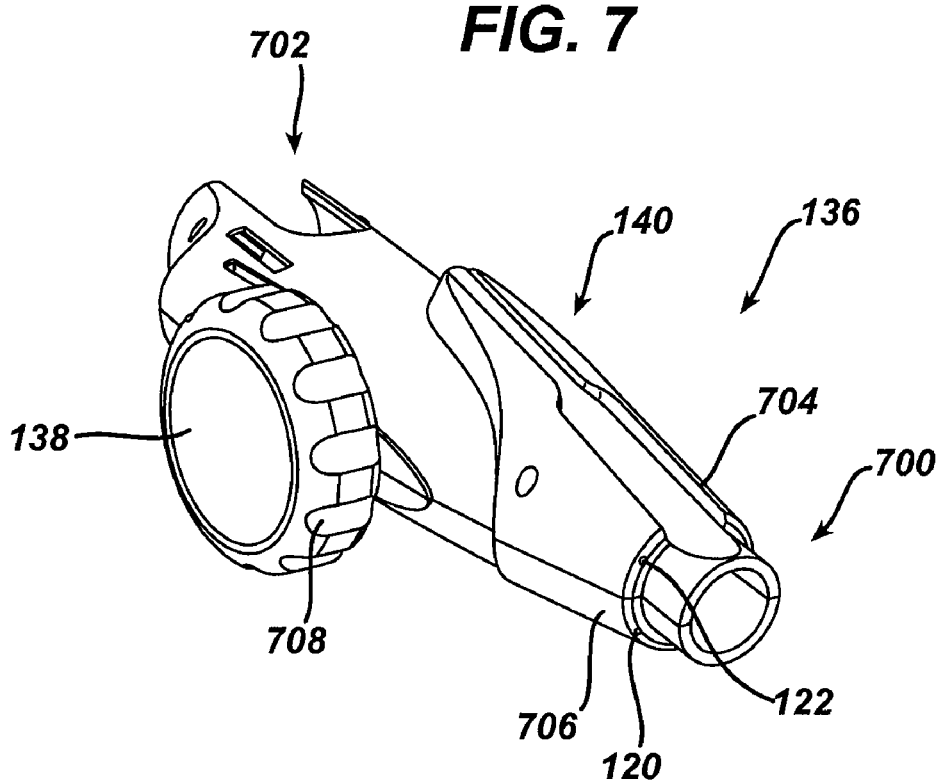
FIG. 7 is a perspective view of the control mechanism of the accessory device shown in FIG. 1.
Figure 8:
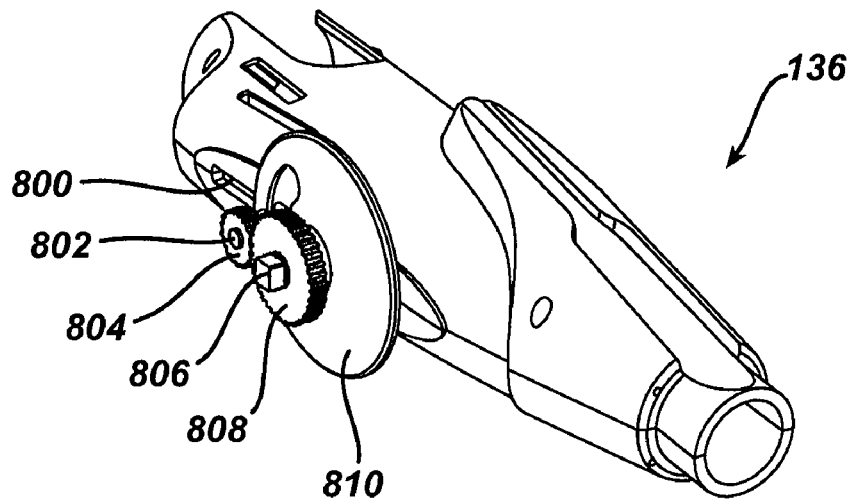
FIG. 8 is a perspective view of the control mechanism shown in FIG. 7 with the knob removed.
Figure 9:
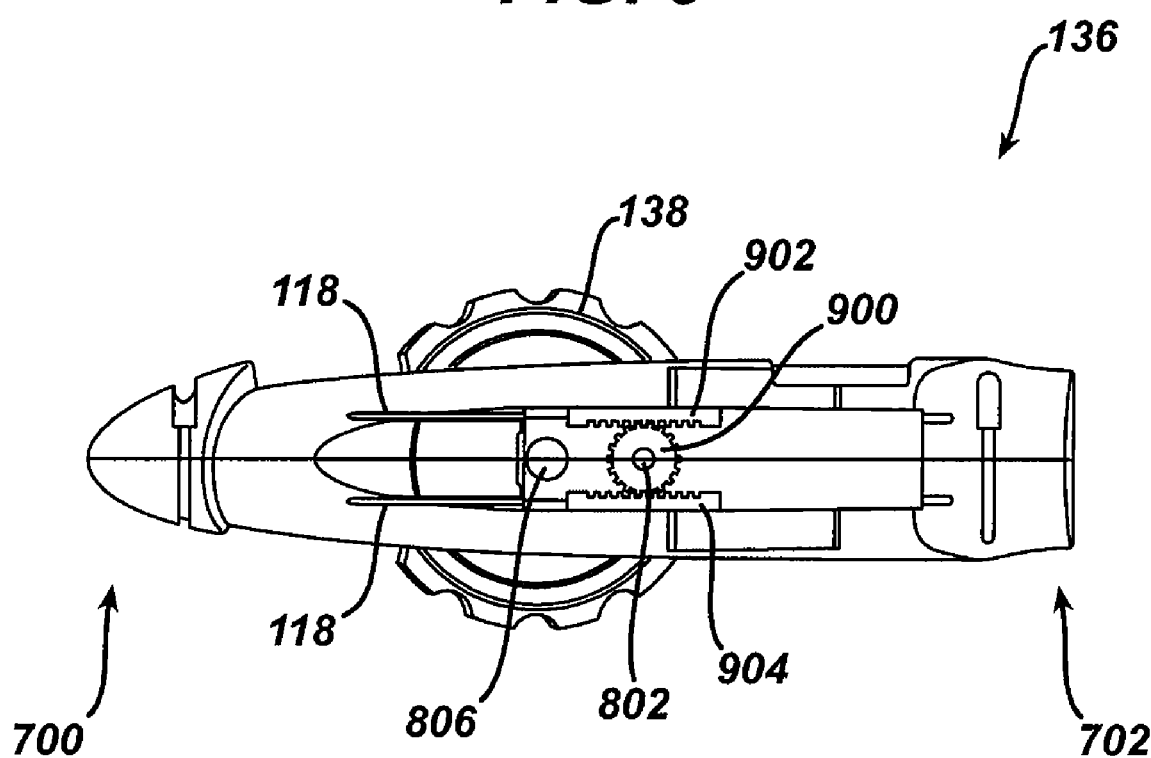
FIG. 9 is a cutaway side view of the control mechanism shown in FIG. 7.

As previously mentioned, the accessory device 100 of FIG. 1 can have a control mechanism 136 disposed on a proximal handle 142. The control mechanism 136 can be located on any portion of the accessory device 100, preferably on a portion that remains outside of the body when the accessory device 100 is used, and/or can be integrated into virtually any part of the accessory device 100. In addition, the control mechanism 136 can be remote to the accessory device 100, connected via a cable, wireless communications path, computer network, and so on. The control mechanism 136 can have a wide variety of configurations, but as shown in FIG. 7 the control mechanism 136 has a body 140 including a top cover 704 and a bottom cover 706 and is adapted to mate with a handle 142 at a proximal end of the elongate sheath 110. The body 140 can have virtually any size and shape and can include indentations, moldings, handles, bar grips, rings, loops, or other accommodations to allow a user to grasp or operate the control mechanism 136. The control mechanism 136 can include any of a wide array of controls, including levers, scissors grips, pivot grips, sliding elements, buttons, dials, switches, pressure sensors, and so on, for manipulating the control wire 118. As shown in an exemplary embodiment in FIG. 7, the control mechanism 136 has a rotatable knob 138 with gripping indentations 708 formed thereon. In FIG. 8 the knob 138 has been removed to show a first shaft 806 about which the knob 138 can rotate and gears 804, 808 which can transfer the force of rotation of the knob 138 to the control wire 118 via a second shaft 802. Although the gears 804, 808 can have virtually any size and gear ratio, the gears 804, 808 can be chosen in light of the desired force required to actuate the knob 138 and/or the degree of control and sensitivity desired in the control mechanism 136. The position of the knob 138 can be adjustable along the rectangular slot 800 shown in FIG. 8. FIG. 9 is a cutaway view of the control mechanism 136 and shows the second shaft 802 coupled to a pinion gear 900 disposed between two racks 902, 904. The upper rack 902 is in turn coupled to the control wire 118, while the lower rack 904 is coupled to the other end of the control wire 118. In other embodiments, one of the racks 902, 904 can be stationary, both ends of the control wire can be coupled to the one of the racks 902, 904, etc. In use, rotation of the knob 138, e.g., can effect axial movement of the control wire 118 within one or more control wire lumens 120, 122 with a mechanical advantage defined by the gear ratios between the knob 138 and the control wire 118. For example, rotation of the knob 138 can move the upper rack 902 distally while moving the bottom rack 904 proximally. In addition, the knob 138 can be coupled to the racks 902, 904 or the control wire 118 such that movement of the knob 138 along slot 800, e.g., by longitudinally sliding the knob 138, can move both racks 902, 904 proximally or distally at the same time and thus move a portion of the control wire 118 disposed in control wire lumen 120 in the same direction as a portion of the control wire 118 disposed in control wire lumen 122.

As one skilled in the art will recognize, many types of actuating mechanisms can be used in place of or in addition to the gears and racks shown in FIGS. 8-9. For example, any type and number of gears can be used, including worm gears, hypoid gears, spur gears, bevel gears, helical gears, annular gears, etc. The control mechanism 136 can have a ratchet or rack and pawl for moving the control wire 118, and/or pressure driven or pressure assisted mechanisms, including gas and fluid systems. The control mechanism 136 can also have actuating rods for pulling and/or pushing the control wire within one or more control wire lumens 120, 122, and winding spools for winding the control wire 118 or another cable or wire which can be coupled to the control wire 118. In addition, the control mechanism 136 can employ electromechanical (e.g., electric motors, magnets, etc.) devices and/or computer-driven or computer-assisted devices for moving the control wire 118. Any of the aforementioned mechanisms can be arranged to move or axially slide the control wire 118 in one or more control wire lumens 120, 122. In some cases, it can be desirable to axially rotate the control wire 118 in order to manipulate a distal portion of the control wire 118. The control mechanism 136 can be coupled to the control wire 118 in a variety of ways. In FIG. 9 the control mechanism 136 is shown coupled to each of two ends of the control wire 118. The control mechanism 136 can be adapted to move just one end of the control wire 118, for example where the opposing send of the control wire 118 is fixedly attached to the elongate sheath 110 or elsewhere.

The accessory device 100 of FIG. 1, as well as any other exemplary accessory devices previously described, can have a variety of other configurations, as one skilled in the art will understand. For example, the accessory device 100 can have multiple accessory channels, lumens for receiving tools, and/or elongate sheaths. On the other hand, the accessory device 100 need not receive a tool, and instead the control wire 118 can be adapted to manipulate a tool inserted separately to the surgical site within the body. Any of the previously described lumens, such as accessory channel lumen 111' in FIG. 2 and/or endoscope lumen 116 in FIG. 1, can receive surgical materials, irrigating fluids, antiseptic agents, or organic substances, etc., therethrough in addition to or instead of tools. The accessory device 100 can have multiple control wires which can be movable within control wire lumens and/or fixedly attached to the accessory device 100. The control wires can be arranged to provide multiple loops or arcs at the distal end of the accessory device 100, and/or can be arranged in a fashion similar to that of a single control wire. In some embodiments, control wire lumens can be associated with the accessory channel instead of or in additional to elongate sheath. A wide array of further variations will be apparent to those skilled in the art.

The present invention also provides methods for manipulating a tool. In one exemplary method, an accessory device such as the accessory device 100 shown in FIG. 1 can be positioned at a surgical site. The accessory device 100 can be positioned in the body by inserting the distal end of the accessory device 100 into a natural orifice such as the mouth, or through an incision made in the body. The accessory device 100 can be advanced distally through a body lumen to a desired position. The insertion may be associated with or preceded by any number of procedures to lubricate, flex, shape, measure, steer, turn, rotate, and/or guide the accessory device 100 into the body. The insertion may also be assisted by or performed with a viewing instrument such as an endoscope for showing the path of the accessory device 100 within the body.

In other embodiments, inserting the accessory device 100 can include inserting an endoscope through an elongate sheath 110, and mating an accessory channel 111 to an elongate sheath 110. For example, as shown in FIGS. 1-2, the rail 152 of the accessory channel 111 can be slidably mated to the track 134 of the elongate sheath 110, and the accessory channel 111 can be advanced to a desired position along the elongate sheath 110. Such mating can be performed at any time, including before and after part of the accessory device 100 is inserted in the body. After it is mated, the accessory channel 111 can be unmated, e.g., by sliding the accessory channel 111 proximally along the elongate shaft 110, and re-mated any number of times to re-introduce the accessory channel 111 or to introduce other accessory channels.

Surgical tools as well as materials can be inserted through one or more lumens in the accessory device 100. For example, a tool can be inserted through the elongate sheath 110, through a lumen 116 formed in an endoscope 130 disposed in the elongate sheath 110, and/or through the accessory channel 111. Multiple tools can be inserted through a single lumen or through separate lumens. Moreover, as will be apparent to those skilled in the art, a tool can also be inserted into the body separately from the accessory device 100, for example, not through any lumen formed therein. A tool can be advanced beyond the distal end 112 of the elongate sheath 110 and can be positioned, articulated, and maneuvered at the surgical site, as may be called for by a surgical procedure.

A surgical tool can be manipulated by the control wire 118. A wide variety of techniques can be used. Such manipulations can effect movement of virtually any nature and direction in the surgical tool. In one exemplary embodiment, however, the tool can be advanced such that at least a distal end of the tool extends between the control wire 118 and the distal end 112 of the elongate sheath 110, or at least a distal end of the tool is received in a loop formed in the control wire 118 itself. The control wire 118 can be used to pull at least a distal end of the tool downwards from the lumen 116. For example, as shown in FIG. 4, the control wire 118 can be used to pull at least a distal end of a tool 410 downwards from the accessory channel lumen 111' towards dotted line 400. Such downward manipulation can bring at least the distal end of the tool within a viewing window of an endoscope. The control wire can 118 also be used to push at least a distal end of the tool distally away from the accessory device 100. Pushing a tool can be facilitated with control wires having loops and/or configurations providing suitable rigidity, for example, as previously discussed and illustrated with respect to FIGS. 6B, 6D. In addition, the control wire 118 can be used to provide a lateral force on the tool. Such a lateral force can move at least the distal end of the tool laterally with respect to a longitudinal axis of the accessory device 100. (For example, an exemplary longitudinal axis is shown as dotted line 400 in FIG. 4.) These and other movements of a surgical tool can be achieved by manipulating the control wire 118 in a variety of ways. For example, axially sliding the control wire 118 within one or both of the control wire lumens 120, 122 can lengthen or shorten a distal portion of the control wire 118 and/or can translate the arc formed by the control wire 118. Sliding the control wire 118 in control wire lumen 120 while keeping the control wire 118 stationary in control wire lumen 122 can effect asymmetrical movement of the control wire 118, or can be useful with a control wire having first and second hooks such as was discussed and shown in FIG. 6C. The control wire 118 can also be turned or rotated in one or both of the control wire lumens 120, 122. In some embodiments, a control mechanism 136 can be used to manipulate the control wire 118. For example, a user can rotate knob 138 to move one end of the control wire distally and move the other end of the control wire 118 proximally, as previously mentioned with respect to FIGS. 8-9. A user can also move the knob 138 longitudinally along slot 800 to move a portion of the control wire 118 in control wire lumen 120 in the same direction, e.g., proximally or distally, as a portion of the control wire 118 in the control wire lumen 122. Such movement can translate an arc or a loop formed in the control wire 118 with respect to the accessory device 100.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

Preferably, the invention described herein will be processed before surgery. First, a new or used tool is obtained and if necessary cleaned. The tool can then be sterilized. In one sterilization technique, the tool is placed in a closed and sealed container, such as a plastic or TYVEK bag. The container and tool are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized. This can be done by any number of ways known to those skilled in the art including beta or gamma radiation, ethylene oxide, or steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An accessory device, comprising: an insertion member having at least one lumen adapted to receive a tool therethrough and having first and second control wire lumens formed therein and adapted to slidably receive a control wire; and wherein the control wire is coupled to the insertion member having a first portion extending through the first control wire lumen, a second portion extending through the second control wire lumen, and a distal portion extending between distal ends of the first and second control wire lumens and extending beyond a distal end of the insertion member, the first and second portions of the control wire being independently movable within the first and second control wire lumens to allow the distal portion of the control wire to receive and manipulate a tool extending through and beyond the distal end of the insertion member.

2. The device of claim 1, wherein the control wire is adapted to move a distal end of a tool extending through the insertion member into a viewing window of an endoscope disposed through the insertion member.

3. The device of claim 1, wherein the control wire is adapted to move a distal end of a tool extending through the insertion member laterally with respect to a longitudinal axis of the insertion member.

4. The device of claim 1, wherein the control wire is adapted to push a distal end of a tool extending through the insertion member distally away from the insertion member.

5. The device of claim 1, wherein the insertion member comprises:
an elongate sheath with the at least one lumen extending longitudinally between proximal and distal ends thereof for receiving an endoscope; and
an accessory channel extending longitudinally along the elongate sheath and having a lumen extending longitudinally therethrough for receiving a tool, the accessory channel having a mating element formed on an external surface thereof and adapted to mate with a mating element formed on an external surface of the elongate sheath,
wherein the distal portion of the control wire that extends from the distal end of the insertion member is adapted to receive and manipulate a tool extending through the lumen of the accessory channel.

6. The device of claim 5, wherein the mating element of the accessory channel includes a rail adapted to mate to a track on the elongate sheath.

7. The device of claim 1, wherein the distal portion of the control wire is in the form of an arc.

8. The device of claim 1, wherein the distal portion of the control wire includes a loop formed therein adapted to receive the tool therethrough.

9. The device of claim 1, further comprising a control mechanism disposed on a handle coupled to a proximal end of the insertion member, the control mechanism being operatively associated with the control wire for axially moving the control wire.

10. The device of claim 1, wherein at least one of the first and second control wire lumens includes a ramp formed therein for directing the control wire towards a tool extending through the insertion member as it exits the at least one of the first second control wire lumens.

11. An endoscopic system, comprising:
an elongate sheath having a first lumen extending longitudinally between proximal and distal ends thereof for receiving an endoscope therein, and first and second engagement mechanism lumens formed therein;
an engagement mechanism extending from the distal end of the elongate sheath and having at least one opening formed therein for receiving a tool, the engagement mechanism having a first portion slidably received in the first engagement mechanism lumen and a second portion slidably received in the second engagement mechanism lumen, the first and second portions of the engagement mechanism having proximal ends that are movable relative to one another, and the engagement mechanism having a distal portion extending between distal ends the first and second engagement mechanism lumens; and
an accessory channel having a mating element formed on an external surface thereof and adapted to couple to a mating element formed on an external surface of the elongate sheath and having a lumen extending longitudinally therethrough for receiving a tool therethrough, the at least one opening of the engagement mechanism being adapted to receive and manipulate a tool extending distally from the lumen of the accessory channel.

12. The system of claim 11, wherein the engagement mechanism has a loop formed therein and adapted to receive a tool therethrough.

13. The system of claim 11, wherein the accessory channel is slidably mated to the elongate sheath.

14. The system of claim 11, further comprising a control mechanism disposed on a handle coupled to the proximal end of the elongate sheath, the control mechanism being operatively associated with the engagement mechanism for axially moving the engagement mechanism relative to the elongate sheath.

15. The system of claim 11, wherein the engagement mechanism comprises a wire.

16. A method for positioning a tool, comprising:
advancing a tool longitudinally along an endoscope to position a distal end of the tool through an opening formed by a control wire extending distally from the endoscope from a first control wire lumen to a second control wire lumen; and
slidably moving first and second portions of the control wire through the first and second control wire lumens to cause the control wire to move the tool relative to the endoscope.

17. The method of claim 16, wherein the tool is advanced through a lumen formed in an accessory channel coupled to the endoscope.

18. The method of claim 16, wherein the endoscope is disposed through an elongate sheath having a control wire lumen formed therein, and manipulating the control wire comprises axially moving the control wire through the control wire lumen in the elongate sheath.

19. The method of claim 16, wherein the manipulation of the control wire to move the tool relative to the endoscope includes contacting the tool with the control wire.

20. The method of claim 16, wherein the first and second portions are slidably moved independent of one another.

* * * * *